(12) United States Patent
Nakamura

(10) Patent No.: US 6,754,914 B2
(45) Date of Patent: Jun. 29, 2004

(54) DISPOSABLE TOILET BOWL FOR CARE

(76) Inventor: Eizou Nakamura, 2-9-26, Sakae-cho, Mito-shi, Ibaraki (JP)

(*) Notice: Subject to any disclaimer, the term of this patent is extended or adjusted under 35 U.S.C. 154(b) by 0 days.

(21) Appl. No.: 10/642,308

(22) Filed: Aug. 18, 2003

(65) Prior Publication Data

US 2004/0093665 A1 May 20, 2004

(30) Foreign Application Priority Data

Nov. 14, 2002 (JP) ........................................ 2002-330220

(51) Int. Cl.⁷ .......................... A47K 11/02; A47K 11/00
(52) U.S. Cl. .............................. 4/449; 4/144.1; 4/144.3; 604/327
(58) Field of Search ............................. 4/144.1–144.4, 4/114.1, 449; 604/327–332, 338, 339, 340, 345

(56) References Cited

U.S. PATENT DOCUMENTS

| | | | | |
|---|---|---|---|---|
| 3,194,238 A | * | 7/1965 | Breece, Jr. ................... | 604/329 |
| 3,556,102 A | * | 1/1971 | Davis ......................... | 604/329 |
| 4,030,500 A | * | 6/1977 | Ronnquist ................... | 604/328 |
| 4,326,521 A | * | 4/1982 | Marsan ....................... | 604/342 |
| 4,457,314 A | * | 7/1984 | Knowles ..................... | 600/573 |
| 4,889,533 A | * | 12/1989 | Beecher ...................... | 604/330 |
| 4,911,698 A | * | 3/1990 | Wapner ....................... | 604/329 |
| 5,125,118 A | * | 6/1992 | Green ......................... | 4/144.2 |
| 5,209,744 A | * | 5/1993 | Abe et al. ................... | 604/342 |
| 5,741,239 A | * | 4/1998 | Mulholland ................. | 604/328 |

* cited by examiner

Primary Examiner—Gregory L. Huson
Assistant Examiner—Khoa Huynh
(74) Attorney, Agent, or Firm—McIntyre-Lilley Intellectual Property Management Services; Richard H. Lilley, Jr.

(57) ABSTRACT

A disposable toilet bowl for care comprises: a rod-like anus application member 3 which fits into a groove 20 between the buttocks 19 around a person's anus 17 and is filled with a fluid; an excrements passage hole 4 which is provided so as to extend through the center of the anus application member 3 and one end of which is applied to the anus 17 when the anus application member 3 is fitted into the groove 20 between the buttocks 19; a flexible sheet-like pad 8 which supports the anus application member 3 from the bottom thereof; fixing means provided on the pad 8 for holding the state that said anus application member 3 is fitted into the groove 20 between the buttocks 19; and a bag body 15 which is communicated with the excrements passage hole 4, of which upper end edge is fixed around the central hole 9 of the pad 8, and which receives internally the excrements discharged from the person's anus 17 through the excrements passage hole 4 and the hole 9 of the pad 8.

1 Claim, 3 Drawing Sheets

DISPOSABLE TOILET BOWL FOR CARE

BACKGROUND OF THE INVENTION

1. Field of the Invention

The present invention relates to a disposable toilet bowl for care which is worn on the body of a person such as the weak old or the invalid person who cannot treat excrements discharged by him (her) self, and which allows a care giving person to treat excrements cleanly and easily when the person discharged excrements.

2. Description of the Related Art

When caring a person such as the weak old or the invalid person who cannot treat excrements discharged by him (her) self (hereinafter, referred to as "a serious person requiring care"), one of the most difficult works is treatment of excrements. The excrements not only give off bad smell, but causes soreness and itchiness when they are adhered to the body, and they also become the cause of giving pain to the serious person requiring care.

Heretofore, in treatment of excrements of the serious person requiring care, in the case of the serious person requiring care who can express their wills of the desire to have bowel movement, it is possible to treat excrements by using a toilet bowl which can be used in bed and thereafter keeping clean by wiping the around the anus. However, the toilet bowl must be treated each time, and it is a considerably troublesome part of care.

On the other hand, for the serious person requiring care who cannot express their wills of the desire to have a bowel movement, from the point of view of disposal handiness, many articles of the disposable system in the form which absorbs excrements and urine such as a so-called paper diaper are also used for treatment of excrements. However, in the case of using the so-called paper diaper, the excreted excrements become spread between the paper diaper and skin of the serious person requiring care and the excrements become adhered wide over the skin, thus posing troublesome in treatment when the paper diaper is removed from the serious person requiring care.

Moreover, there has been also proposed a disposable toilet bowl of the type in which a pouch is attached to a part of the anus of the serious person requiring care and excrements are discharged therein. However, since the surroundings of the anus are not flat, a big gap is generated between the disposable toilet bowl and the surrounding skin of the anus. Especially, in the case of loose feces, there are many problems such that when feces leak from the gap, bedclothes, pajamas and the like are spoiled. Actually, disposable toilet bowls have not been developed up to the present, which can be worn without feeling uncomfortable substantially at all times and are hard to leak out feces.

In Japan, a decrease in the birthrate and an aging that have not been experienced by the advanced countries are now developing, and therefore we fear an increasing of the serious persons requiring care and a shortage of care giving persons. In such a situation as described, there has been demanded the way that gives no pain and trouble to the serious person requiring care.

A treatment of the excrements discharged by the serious person requiring care is also one of the ways, and it is required to allow the serious person requiring care to excrete excrements without giving much troubles and pains to the serious person requiring care at any time. To this end, it is desired to develop the disposable toilet bowl that can be worn by the serious person requiring care substantially any time and in which excrements discharged are not adhered to any parts other than the circumference of anus as a result of leakage thereof.

In the view of the problem noted above with respect to the conventional treatment of excrements discharged by the serious person requiring care, it is an object of the present invention to provide a disposable toilet bowl for care which can be worn by the serious person requiring care without sense of incongruity substantially at all time, and in which excrements discharged are not adhered to any parts other than the circumference of anus as a result of leakage thereof.

SUMMARY OF THE INVENTION

For achieving the above-described object, according to the present invention, there is provided an arrangement wherein a rod-like anus-application member 3 which fits into a groove 20 between buttocks 19 around anus 17 in order to lead to a bag body 15 excrements excreted from the anus 17 of the serious person requiring care, and the excretion of excrements is enabled into the bag body 15 through an excrement passage hole 4 provided in the center of the anus application-member 3. While inside the anus application member 3 is filled with a fluid, a flexible sheet-like pad 8 holds the state that the anus application member 3 is fitted into the groove 20 between the buttocks 19, a free deformation and restoring force of the anus application-member 3 allow free following the movement of the buttocks 19 and the groove 20 therebetween, and further the close-contact can be secured.

Thus, the disposable toilet bowl for care according to the present invention comprises the rod-like anus application member 3 which fits into the groove 20 between the buttocks 19 around the person's anus 17 and is filled with the fluid, the excrements passage hole 4 which is provided so as to extend through the center of the anus application member 3 and one end of which is applied to the anus 17 when the anus application member 3 is fitted into the groove 20 between the buttocks 19, the flexible sheet-like pad 8 which supports the anus application member 3 from the bottom thereof, fixing means provided on the pad 8 for holding the state that the anus application member 3 is fitted into the groove 20 between the buttocks 19, the bag body 15 which is communicated with the excrements passage hole 4, of which upper end edge is fixed around a central hole 9 of the pad 8, and which receives internally the excrements excreted from the person's anus 17 through the excrements passage hole 4 and the hole 9 of the pad 8.

In the disposable toilet bowl for care as described above, the anus application member 3 having the excrements passage hole 4 for guiding the excrements discharged from the person's anus 17 to the bag body 15 is internally filled with the fluid, is deformed freely, and is easily returned to the original shape when external force is removed. Thus, the anus application member 3 is held, in the state that the former is fitted into the groove 20 between the buttocks 19 around the person's anus 17, by the flexible sheet-like pad 8, whereby the anus application member 3 is deformed freely to some extent within the groove 20 between the buttocks 19, and can follow freely the movement of the person's buttocks 19 and the groove 20 therebetween. Accordingly, the upper end of the excrements passage hole 4 is not displaced easily from the person's anus 17. Further, since the anus application member 3 is deformed freely and tends to be returned to its original shape when the external force is removed, the anus application member 3 completely comes in close contact with the groove 20 between the buttocks 19 to prevent the excrements from leaking. And the disposable toilet bowl for care can be always worn to receive the excrements discharged from the anus of the serious person requiring care to treat it, and since the disposable toilet bowl containing the excrements therein can be abandoned as it is the treatment of the excrements by the care giving person becomes considerably easy.

DESCRIPTION OF THE PREFERRED EMBODIMENTS

The embodiments of the present invention will be described in concrete and detail hereinafter with reference to the accompanying drawings.

Figure 1:
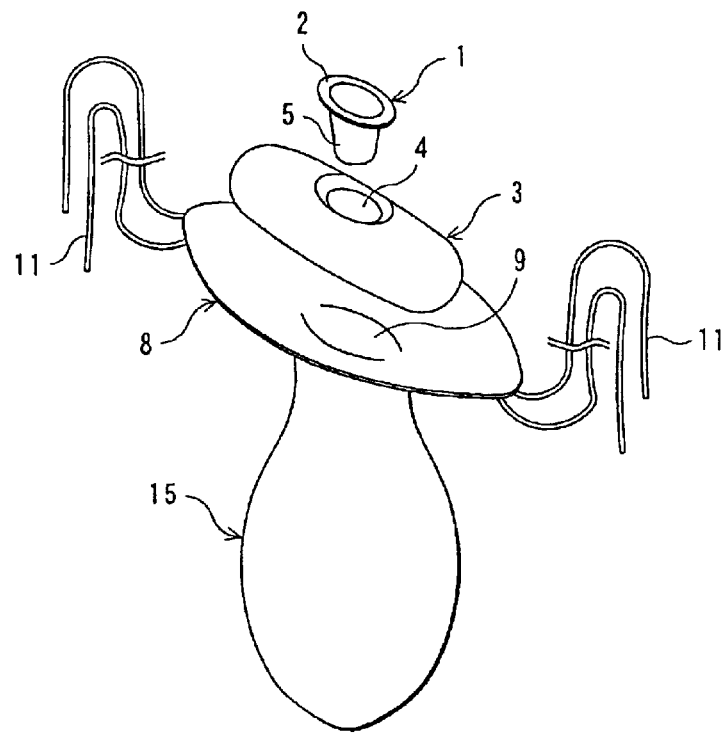
FIG. 1 is an exploded perspective view showing constituent members of a disposable toilet bowl for care according to one embodiment in an exploded form.
Figure 2:
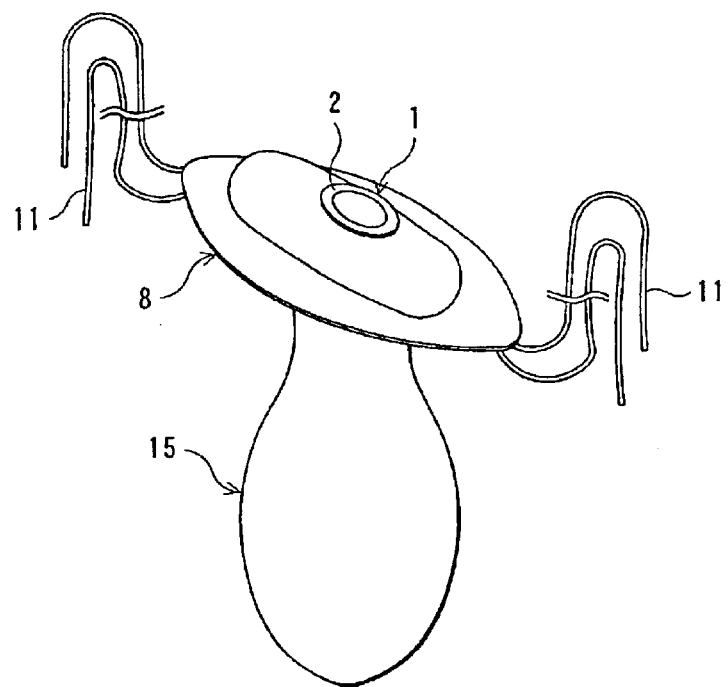
FIG. 2 is a perspective view showing the disposable toilet bowl for care according to the one embodiment.
Figure 3:
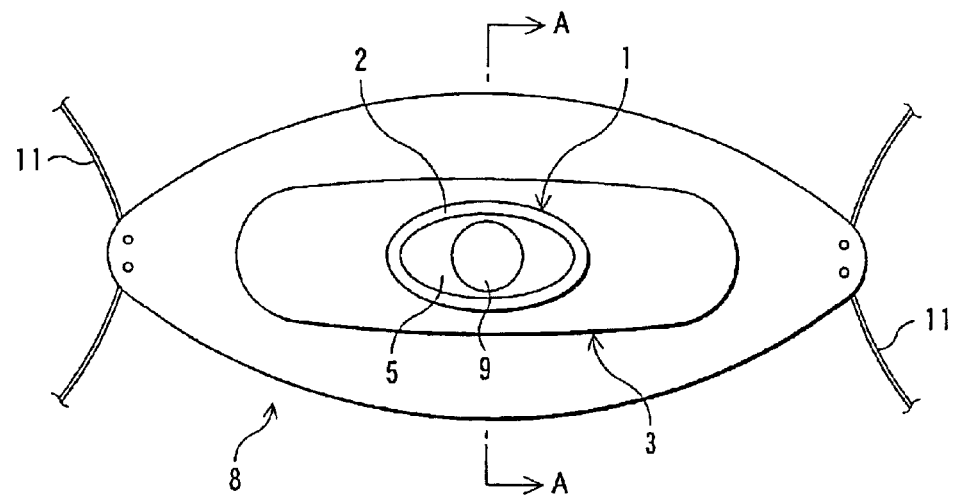
FIG. 3 is a plan view showing the disposable toilet bowl for care according to the one embodiment.
Figure 4:
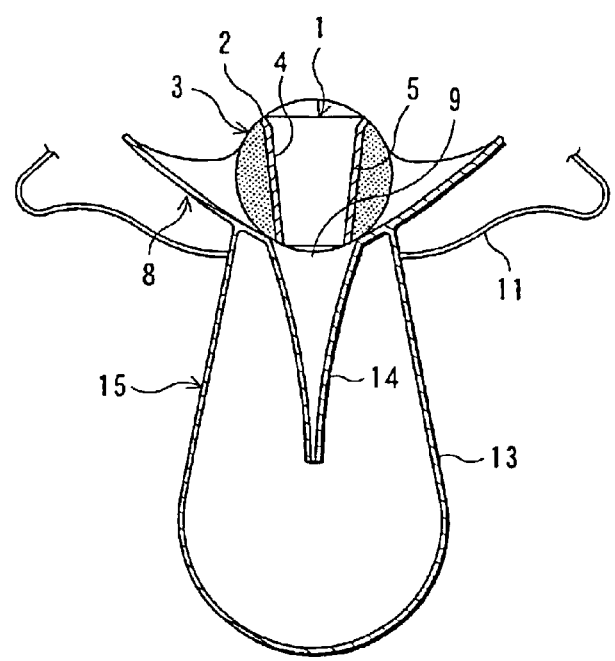
FIG. 4 is a sectional view taken on line A—A of FIG. 3.

FIG. 1 shows constituent members of a disposable toilet bowl for care according to one embodiment of the present invention. FIGS. 2 to 4 show the state that these constituent members are integrated to constitute a disposable toilet bowl for care. As shown in these figures, the disposable toilet bowl for care shown comprises an anus application member 3, a pad 8, and a bag body 15.

The anus application member 3 is a rod-like member having a diameter of about 30 to 40 mm and a length of about 80 to 100 mm, in which a bag having strong expansibility and elasticity formed from an expansible material. For the bag, there is used a member such as soft resin, rubber or the like which gives no strong stimulus on the skin of a person, occurs no allergy or the like, and has air tightness and water resistance. As a fluid to be filled in the bag, there can be mentioned a gas such as air, a liquid such as water or oily liquid, a paste-like material, and a solid such as powder. Anyway, the bag is filled with a fluid under suitable pressure such that when external force is applied to the anus application member 3, its deformation is allowed, whereas when the external force is removed, the bag is returned to its original shape by the elastic force thereof.

The anus application member 3 is provided in the center thereof with an excrements passage hole 4 through which excrements discharged from a person's anus pass. A cylindrical excrements passage pipe 1 is fitted into the excrements passage hole 4. The excrements passage pipe 1 has a flange 2 on the upper end thereof, under which a funnel-like pipe portion 5 is provided integrally. The excrements passage pipe 1 is formed thick by a member having rigidity that is hard to be deformed from the bag which is the cuticle of the anus application member 3. By forming so, even if the anus application member 3 is deformed, the excrements passage pipe 1 and a portion of the excrements passage hole 4 having the former fitted in are not deformed greatly so as to secure a passage through which excrements pass. Where the excrements passage pipe 1 is not used, only the portion of the excrements passage hole 4 of the bag which is the cuticle of the anus application member 3 is formed thick so as to be hard to be deformed from other portions of the bag which is the cuticle of the anus application member 3.

The pad 8 is formed from a flexible sheet having a thickness of about 1 mm, which is in the shape of long oval on one side. This pad 8 has in the center thereof a hole 9 for causing excrements to pass through. Since this pad 8 is also used while being put on the skin around the person's anus, it is preferable to use soft resin or hygroscopic fiber which gives no strong stimulus on the skin of a person, and causes no allergy or the like.

The rod-like anus application member 3 is placed on and fixed to the central portion of the pad 8. In more detail, the anus application member 3 is fixed so that the lengthwise direction thereof coincides with long axial direction of the pad 8. In this condition, the lower end opening of the excrements passage hole 4 of the anus application member 3 vertically coincides with the hole 9 of the pad 8.

On both ends in the long axial direction of the pad 8 are mounted strings 11 as fixing means for mounting the pad 8 on the person's buttocks.

The upper end of the bag body 15 is integrally mounted on the circumference of the hole 9 in the lower surface of the pad 8, and the hole 9 is communicated with the interior of the bag body 15. The bag body 15 is formed from a material which has expansibility and elasticity, tends to be deformed and has water tightness such as rubber, synthetic resin or the like.

As will be apparent from FIG. 4, the bag body 15 in the illustrated embodiment is of a double construction comprising an outer bag 13 and an inner bag 14. The outer bag 13 is a bag in which excrements are being stored, which is a completely closed bag, the upper edge of which is integral with the circumferential portion of the hole 9 of the pad 8. The inner bag 14 is a funnel-like bag in which the upper edge integral with the hole 9 of the pad 8 is wide, and the lower end thereof is narrow, the lower end being opened in the outer bag 13.

Figure 5:
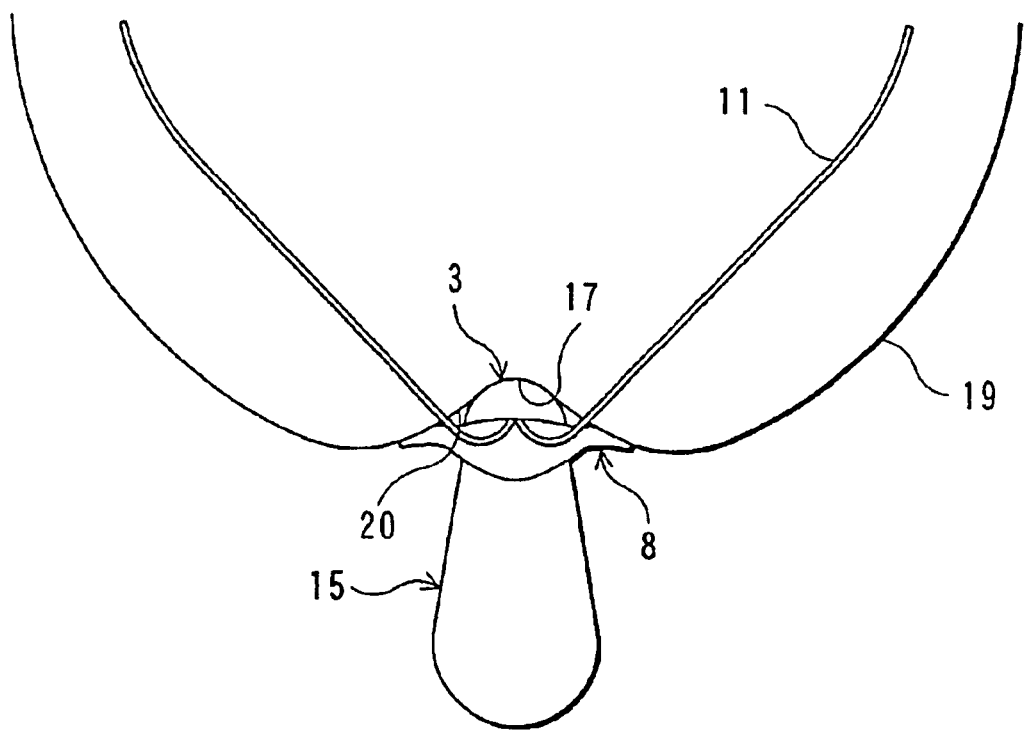
FIG. 5 is a rear view in the state that the disposable toilet bowl for care according to the one embodiment is applied to the person's the buttocks.

The using state of the disposable toilet bowl as described above is shown in FIG. 5. As shown in FIG. 5, the anus application member 3 is fitted into the groove 20 between the buttocks 19 around the person's anus 17, and the upper end of the excrements passage hole 4 in the central portion of the anus application member 3. In this state, strings 11, 11 are put through the back of the person's buttocks and both sides of the thigh, and these strings 11, 11 are tied and the pad 8 is applied and secured to the skin around the anus 17. In this state, the disposable toilet bowl for care is worn on the buttocks of the serious person requiring care.

In the worn state, when the excrements are discharged from the anus 17 of the serious person requiring care, they pass through the excrements passage hole 4 of the rod-like anus application member 3 fitted into the groove 20 around the anus 17, and the excrements are discharged into the bag body 15 from the hole 9 of the pad 8. The excrements first pass through the inner bag 14 of the bag body 15, escape from the lower end thereof, and enter the outer bag 13. The inner bag 14 is funnel-like, the lower end of which is narrower than the upper end, thus serving as means of preventing a back flow.

The anus application member 3 is filled with the fluid so that it is deformed freely to some extent according to the movement of the serious person requiring care, and has the restoring force. Because of this, it is fitted into the groove 20 between the buttocks 19 into close contact with the groove 20. Further, the upper end of the anus application member 3 is not displaced from the anus 17.

As described above, the disposable toilet bowl according to the present invention is always worn by the serious person requiring care, and the excrements discharged from the anus of the serious person requiring care can be received into the bag body 15 for treatment. At this time, the anus application member 3 is filled with the fluid whereby it is deformed according to the movement of the serious person requiring care and has the restoring force, and therefore the excellent close contact and anti-displacement are achieved, there occurring no leakage of excrements. Further, since the disposable toilet bowl containing excrements therein can be abandoned as it is, the treatment of excrements by the care giving person becomes considerably easy.

What is claimed is:

1. A disposable toilet bowl for care for receiving and storing excrements discharged from the anus of a disabled person, comprising:

a rod-like anus application member (3) adapted to fit into a groove (20) between the buttocks (19) and surrounding a person's anus (17) and is filled with a fluid, wherein the filled fluid provides a deformation and restoring force for the anus application member (3) allowing free movement of the buttocks (19) and the groove (20) therebetween;

an excrements passage hole (4) which is provided so as to extend through the center of the anus application member (3) and one end of which is applied to the anus (17) when the anus application member (3) is fitted into the groove (20) between the buttocks (19);

a flexible sheet-like pad (8) which supports the anus application member (3) from the bottom thereof;

fixing means provided on the pad (8) for holding said anus application member (3) about said anus (20) between the buttocks (19);

and a bag body (15) which is communicated with the excrements passage hole (4), of which upper end edge is fixed around the central hole (9) of the pad (8), and which receives internally the excrements discharged from the person's anus (17) through the excrement's passage hole (4) and the hole (9) of the pad (8).

* * * * *